US010307255B1

United States Patent
Hutton et al.

(10) Patent No.: US 10,307,255 B1
(45) Date of Patent: Jun. 4, 2019

(54) ACETABULAR CUP ASSEMBLY

(71) Applicant: b-ONE Ortho, Corp., Cedar Knolls, NJ (US)

(72) Inventors: Clark Hutton, Oceanside, CA (US); Imants Liepins, Asbury, NJ (US)

(73) Assignee: b-ONE Ortho, Corp., Cedar Knolls, NJ (US)

( * ) Notice: Subject to any disclaimer, the term of this patent is extended or adjusted under 35 U.S.C. 154(b) by 79 days.

(21) Appl. No.: 15/825,430

(22) Filed: Nov. 29, 2017

(51) Int. Cl.
*A61F 2/34* (2006.01)
*A61F 2/46* (2006.01)
*A61F 2/30* (2006.01)

(52) U.S. Cl.
CPC .............. *A61F 2/34* (2013.01); *A61F 2/4609* (2013.01); *A61F 2002/30332* (2013.01); *A61F 2002/3411* (2013.01); *A61F 2220/0025* (2013.01); *A61F 2310/00023* (2013.01)

(58) Field of Classification Search
CPC ................................................ A61F 2002/3411
See application file for complete search history.

(56) References Cited

U.S. PATENT DOCUMENTS

| | | | |
|---|---|---|---|
| 5,021,062 A | 6/1991 | Adrey et al. | |
| 5,080,677 A | 1/1992 | Shelley | |
| 5,217,499 A | 6/1993 | Shelley | |
| 5,282,684 A | 2/1994 | Holzer | |
| 5,314,487 A | 5/1994 | Schryver et al. | |
| 5,549,691 A | 8/1996 | Harwin | |
| 5,766,260 A | 6/1998 | Whiteside | |
| 5,782,928 A | 7/1998 | Ries et al. | |
| 5,919,236 A | 7/1999 | Pfaff et al. | |
| 5,925,077 A | 7/1999 | Williamson | |
| 5,935,175 A | 8/1999 | Ostiguy et al. | |
| 5,938,702 A | 8/1999 | Lopez et al. | |
| 6,059,833 A | 5/2000 | Doets | |
| 6,123,729 A | 9/2000 | Insall et al. | |
| 6,129,765 A | 10/2000 | Lopez et al. | |

(Continued)

FOREIGN PATENT DOCUMENTS

EP 0927548 B1 5/2003

OTHER PUBLICATIONS

International Search Report and Written Opinion dated Aug. 29, 2018 for corresponding PCT Application No. PCT/US2018/021024.

*Primary Examiner* — Megan Y Wolf
(74) *Attorney, Agent, or Firm* — Duane Morris LLP

(57) ABSTRACT

An acetabular cup assembly includes a shell and a liner. The shell has an inner surface, an outer surface, a face positioned at an upper end of the shell, and an apex positioned at a lower end of the inner surface. The inner surface includes a tapered inner wall and a plurality of inwardly-facing recesses provided along the inner surface adjacent the face. The plurality of inwardly-facing recesses include a main portion and an asymmetrically-extending portion. Each of the asymmetrically-extending portions extend circumferentially in one direction resulting in the recesses having an asymmetric shape. The segmented portion of the tapered inner wall has a wide portion between the asymmetrically-extending portion and the face and a narrower portion between the asymmetrically-extending portion and the adjacent inwardly-facing recess. The liner is adapted to fit within the shell and engage the inner surface of the shell establishing an interference fit.

21 Claims, 6 Drawing Sheets

(56) References Cited

U.S. PATENT DOCUMENTS

| | | | |
|---|---|---|---|
| 6,132,469 A | 10/2000 | Schroeder | |
| 6,334,875 B1 | 1/2002 | Keller | |
| 6,379,389 B1 | 4/2002 | Koch | |
| 6,475,243 B1 | 11/2002 | Sheldon et al. | |
| 6,537,321 B1 | 3/2003 | Horber | |
| 6,610,097 B2 | 8/2003 | Serbousek et al. | |
| 6,966,932 B1 | 11/2005 | Schroeder | |
| 7,044,974 B2 | 5/2006 | Garber et al. | |
| 7,169,165 B2 | 1/2007 | Sidebotham | |
| RE40,090 E | 2/2008 | Whiteside | |
| 7,326,253 B2 | 2/2008 | Synder et al. | |
| 7,708,783 B2 | 5/2010 | Richards | |
| 6,475,243 C1 | 12/2010 | Sheldon et al. | |
| 7,955,395 B2 | 6/2011 | Shea et al. | |
| 8,002,842 B2 | 8/2011 | Ronk | |
| 8,123,815 B2 | 2/2012 | Meridew et al. | |
| 8,268,383 B2 | 9/2012 | Langhorn | |
| 8,308,810 B2 * | 11/2012 | Meridew | A61F 2/34 623/22.19 |
| 8,308,811 B2 | 11/2012 | Newsome et al. | |
| 8,585,769 B2 | 11/2013 | Vankoski et al. | |
| 8,603,182 B2 | 12/2013 | Lambert et al. | |
| 8,679,187 B2 | 3/2014 | Allen et al. | |
| 8,679,188 B2 | 3/2014 | Shea et al. | |
| 8,771,367 B2 | 7/2014 | Armacost et al. | |
| 8,801,797 B2 | 8/2014 | Imhof | |
| 8,801,798 B1 | 8/2014 | Smith | |
| 8,900,319 B2 | 12/2014 | Morrey et al. | |
| 9,005,302 B2 | 4/2015 | Brehm | |
| 9,144,497 B2 | 9/2015 | Sun et al. | |
| 9,168,142 B2 | 10/2015 | Alley et al. | |
| 9,180,013 B2 | 11/2015 | Grostefon et al. | |
| 9,358,118 B2 | 6/2016 | Farrar et al. | |
| 9,463,093 B2 | 10/2016 | Allen et al. | |
| 9,463,094 B2 | 10/2016 | Allen et al. | |
| 9,468,529 B2 | 10/2016 | Smith | |
| 9,713,531 B2 | 7/2017 | Grostefon et al. | |
| 2005/0137710 A1 | 6/2005 | Steinberg | |
| 2005/0177244 A1 | 8/2005 | Steinberg | |
| 2006/0190089 A1 | 8/2006 | Montoya et al. | |
| 2006/0229731 A1 | 10/2006 | Newsome et al. | |
| 2007/0106392 A1 | 5/2007 | Servidio et al. | |
| 2007/0203583 A1 | 8/2007 | Slone | |
| 2007/0219562 A1 * | 9/2007 | Slone | A61F 2/34 606/99 |
| 2016/0022424 A1 | 1/2016 | Grostefon et al. | |
| 2016/0135958 A1 | 5/2016 | Grostefon et al. | |
| 2016/0213478 A1 | 7/2016 | Morrey et al. | |
| 2016/0262900 A1 | 9/2016 | Otto et al. | |
| 2017/0020688 A1 | 1/2017 | Allen et al. | |
| 2017/0086980 A1 | 3/2017 | Suckow | |

* cited by examiner

ACETABULAR CUP ASSEMBLY

FIELD

The invention relates to acetabular cups, specifically to acetabular cups having a shell and a liner.

BACKGROUND

Orthopedic implants are increasingly being used to treat degenerative diseases and other conditions that affect hip, knee, shoulder and other joint function. One prevalent use of orthopedic implants is for hip replacement surgeries. The hip joint is made up of the spherical head of the femur and the cup-shaped acetabulum of the pelvis. For replacement of the hip joint, a stem is inserted into the femur. On the proximal end of the stem, a ball replicates the spherical head of the femur. A cup is implanted into the pelvis to replicate the acetabulum. The cup is often made of a shell that is implanted into the pelvis and a liner that sits within the interior of the shell and provides a bearing surface for the ball.

SUMMARY

An acetabular cup assembly according to the present disclosure comprises a shell, the shell having an inner surface defining an interior space, an outer surface defining an outer surface, a face positioned at an upper end of the shell, and an apex positioned at a lower end of the inner surface. The inner surface comprises a tapered inner wall extending from the face toward the apex; a plurality of inwardly-facing recesses provided along the inner surface adjacent the face; a concave portion defined between the tapered inner wall and the apex; and a liner adapted to fit within the interior space and engage the inner surface of the shell establishing an interference fit. The plurality of inwardly-facing recesses have a main portion and an asymmetrically-extending portion and interrupt the tapered inner wall. The plurality of inwardly-facing recesses also define a segmented portion of the tapered inner wall between each pair of adjacent inwardly-facing recesses. Each of the asymmetrically-extending portion extends circumferentially in one direction and is spaced apart from the face resulting in the recesses having an asymmetric shape and the segmented portion of the tapered inner wall has a wide portion between the asymmetrically-extending portion and the face and a narrower portion between the asymmetrically-extending portion and the adjacent inwardly-facing recess.

A method for implanting an acetabular cup is also disclosed. The method comprises the steps of:

providing a shell member having an inner surface defining an interior space and a central axis, an outer surface defining an outer hemispherical surface, a face positioned at an upper end of the shell, and an apex positioned at a lower end of the inner surface, the inner surface comprising a tapered inner wall extending axially, a concave portion defined between the tapered inner wall and the apex, and an annular groove provided between the tapered inner wall and the concave portion and extending at least partially around the inner surface; wherein the tapered inner wall has an inner diameter, at a predefined contact point that is 0.5 to 3.0 mm from the annular groove, that is same as the outside diameter of the annular rib of the liner;

providing a liner for axial securement within the internal cavity and having a central liner axis, an outer surface that is configured with a male tapered surface that is compatible with the tapered inner wall, the liner having an annular rib provided at the bottom end of the male tapered surface for being received into the annular groove of the shell member, the central axis coinciding with the central liner axis when the shell member and the liner are assembled;

centering the liner in the shell member by inserting the liner in axial direction into the interior space of the shell member until the annular rib of the liner engages the tapered inner wall of the shell before the annular rib snaps into the annular groove of the shell member; and securing the liner within the shell member by further inserting the liner in axial direction into the interior space of the shell member until the annular rib snaps into the annular groove of the shell member.

BRIEF DESCRIPTION OF THE DRAWINGS

These and other features and advantages of the present invention will be more fully disclosed in, or rendered obvious by, the following detailed description of the preferred embodiment of the invention, which is to be considered together with the accompanying drawings wherein like numbers refer to like parts and further wherein.

DETAILED DESCRIPTION

Figure 1:
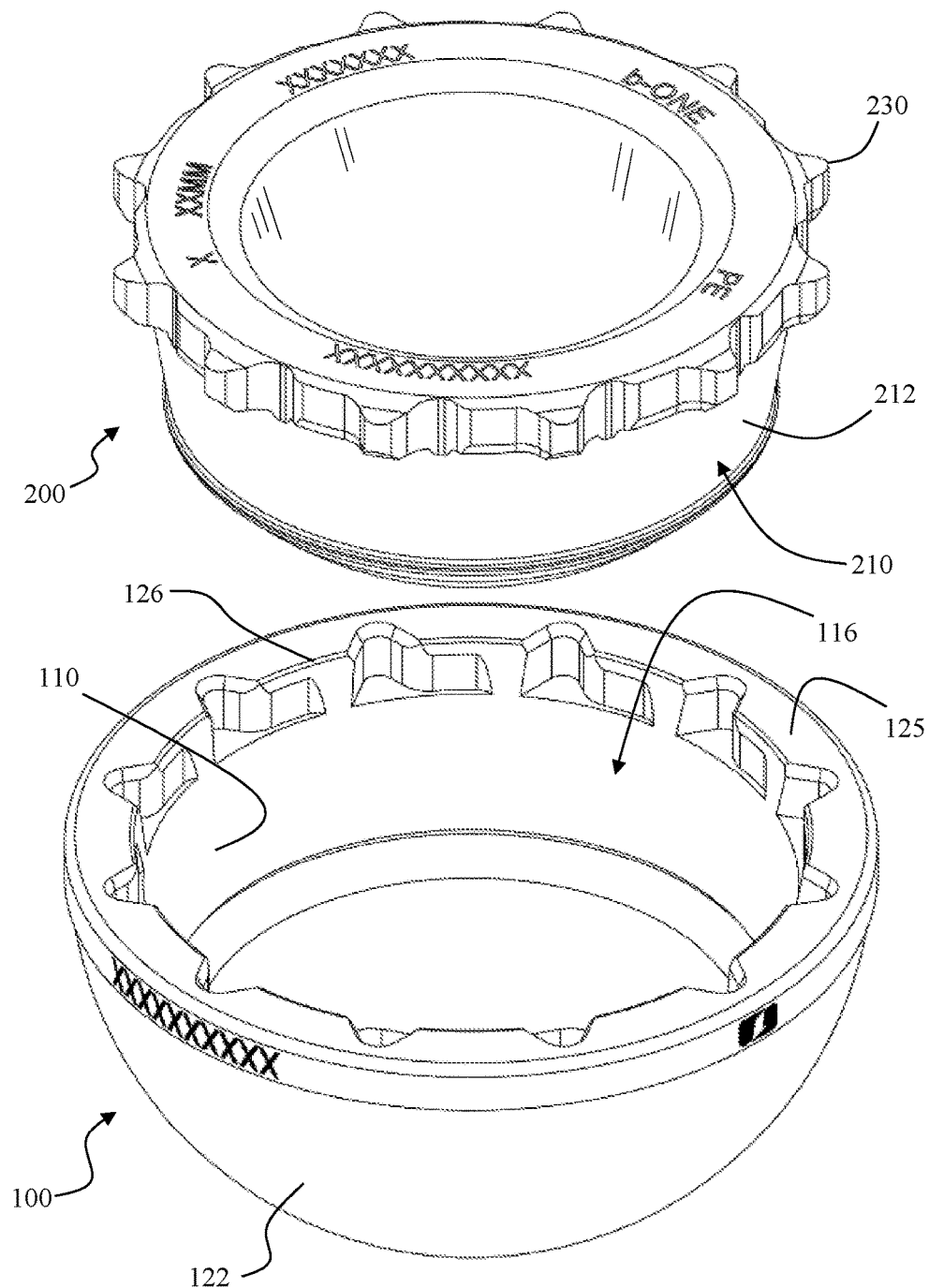
FIG. 1 shows a perspective view of an acetabular shell component of the acetabular cup implant system.
Figure 2:
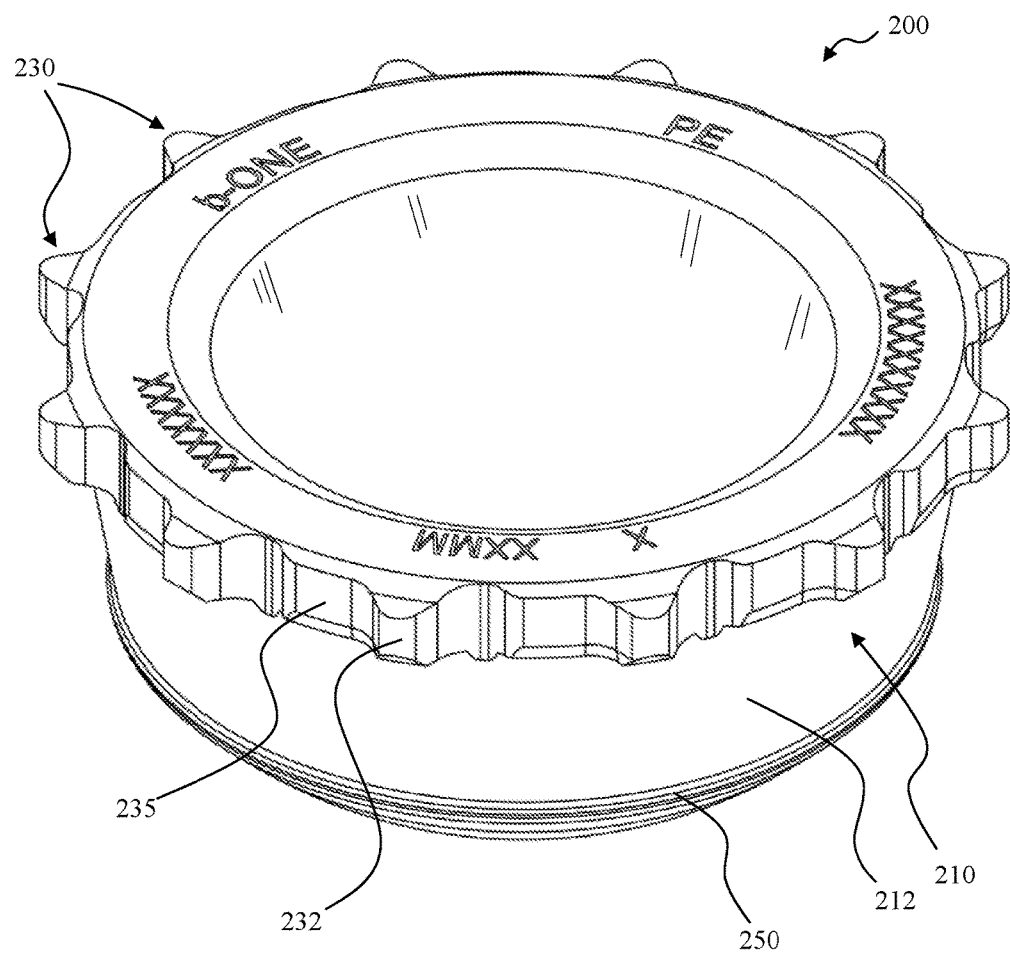
FIG. 2 shows a perspective view of a liner component of the acetabular cup implant system.

This description of preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively or operably connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

The present disclosure describes an acetabular cup assembly that can be used in hip replacement surgeries. As described further with reference to the embodiments herein, the acetabular cup includes a shell and a liner. The shell and the liner include features to ensure that the liner is secured to the shell and that relative movement therebetween is limited. The liner can be configured to serve as a bearing for a ball of a femur implant. The shell and liner can be provided in multiple sizes to allow the physician to choose the appropriate size based on the patient's anatomy. The shell can be compatible with multiple liners. For example, a single shell can be compatible with a ceramic liner, a polymeric liner, a metal liner, and liners of other suitable material.

In one embodiment, as shown in FIG. 1, the acetabular cup assembly has a shell 100 and a liner 200. The shell 100 has an inner surface 110 defining an interior space 116. The shell 100 also includes an outer surface 122, which can take the form of a convex surface and can define a hemispherical surface. The shell 100 also includes a face 125 positioned at an upper end of the shell 100.

The shell can be constructed of any appropriate material. For example, the shell 100 can be constructed from titanium, cobalt chromium, stainless steel, or other biocompatible material. Additionally, the outer surface of the shell 100 can be coated with a coating that improves bone ingrowth or improves the retention of the shell 100 in the acetabulum. For example, the coating can be a porous coating. The coating can be a sintered metal coating, a vapor deposited metal coating, a thermal spray metal coating, or be chemically etched.

Figure 3:
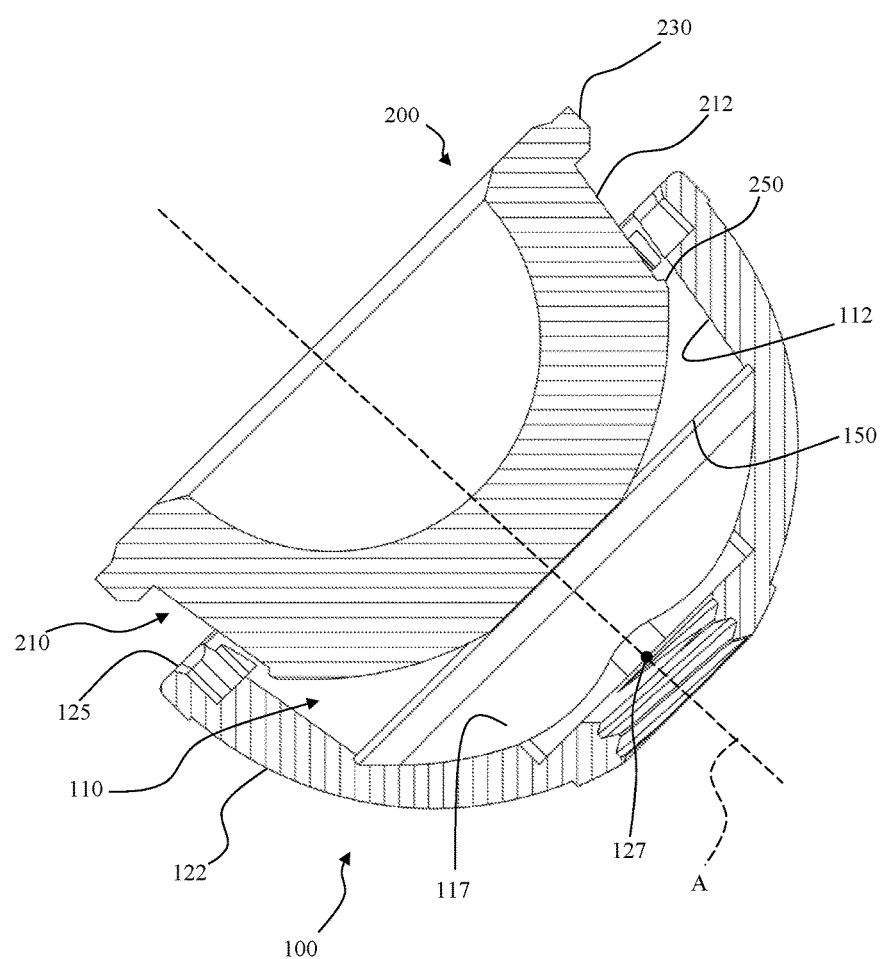
FIG. 3 shows an exploded axial cross-sectional view of the acetabular cup implant system of the present disclosure.

As shown in FIG. 3, the shell 100 and the liner 200 are symmetric about a central axis A of the assembly. The inner surface 110 of the shell 100 includes a tapered inner wall 112 portion extending from the face 125 toward the apex 127. The tapered inner wall is tapered at a first taper angle with respect to the central axis A.

The liner 200 is adapted to fit within the interior space of the shell 100 and engage the inner surface 110 of the shell 100 and establish an interference fit therebetween. The liner has an outer surface 210 with a male tapered surface 212 portion that is tapered at a second taper angle with respect to the central axis of the liner. The male tapered surface 212 is configured to engage the tapered inner wall 112 portion of the shell 100. The taper angles of the shell and the liner are selected to promote secure engagement of the two components. In one embodiment, the first taper angle and the second taper angle are approximately the same as the first taper angle. In another embodiment, the second taper angle is greater than the first taper angle. In one embodiment, the first and taper angles are approximately 18°.

The corner or the edge 126 where the tapered inner wall 112 portion and the face 125 of the shell 100 meet is chamfered, The chamfered edge 126 can help guide the insertion of the liner 200 into the shell 100.

Figure 4:
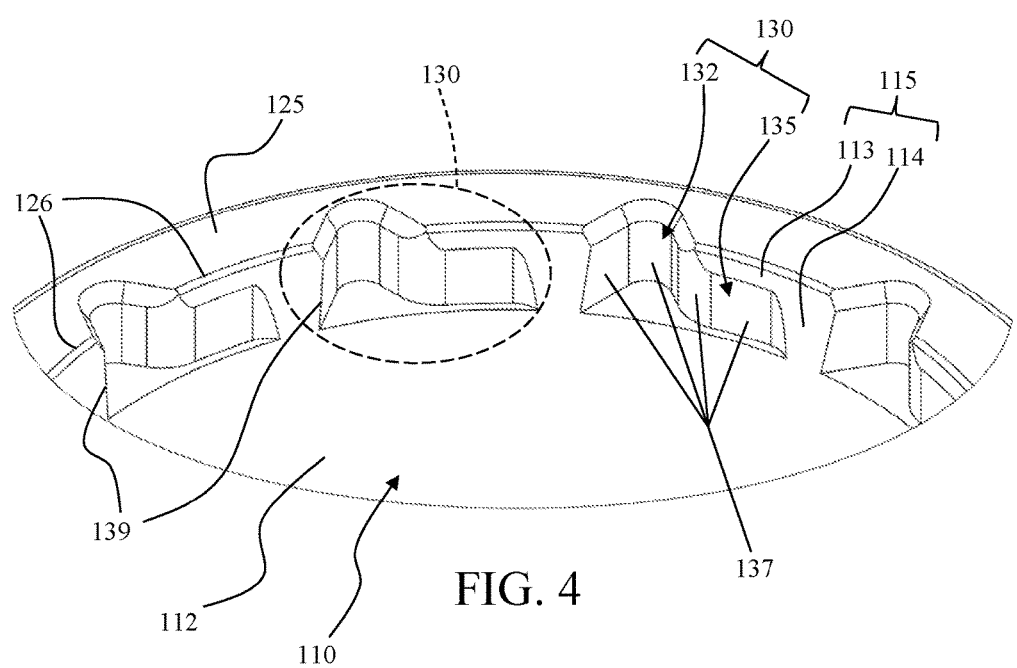
FIG. 4 shows a detailed view of a portion of the acetabular shell component.

Referring to FIG. 4, the inner surface 110 of the shell 100 also includes a plurality of inwardly-facing recesses 130 provided along the inner surface 110 adjacent the face 125. The plurality of inwardly-facing recesses 130 have a main portion 132 and an asymmetrically-extending portion 135. The inwardly-facing recesses are provided for securement of the shell 100 and the liner 200 and the main portion 132 of the inwardly-facing recesses 130 is configured to receive a radial projection 230 (described below) of the liner 200.

The inwardly-facing recesses 130 interrupt the tapered inner wall 112 and define a segmented portion 115 of the tapered inner wall 112 between each pair of adjacent inwardly-facing recesses 130. The function of the inwardly-facing recesses 130 will be discussed in more detail below.

Each of the asymmetrically-extending portions 135 extend circumferentially in one direction. As will be described in more detail below, the asymmetrically-extending portions 135 provide additional means for establishing securement between the shell 100 and the liner 200 by providing interference fitting between the shell and the liner that supplements the locking engagement provided by the annular groove 150 of the shell and the annular rib 250 of the liner described below.

The asymmetric configuration of the recesses 130 allows provision of the additional interference fitting mechanism between the shell 100 and the liner 200 without sacrificing too much of the tapered inner wall 112 surface. This provides more engagement of the corresponding tapered surfaces between the shell 100 and a ceramic liner which engages the shell via the tapered surfaces only.

In addition, the asymmetrically-extending portions 135 do not extend up to the chamfered edge 126. Hence, a portion of the tapered inner wall 112 between the face 125 and each of the asymmetrically-extending portion 135 form a part of the segmented portion 115 which is a wide portion 113. As a result, the segmented portion 115 of the tapered inner wall has the wide portion 113 between the asymmetrically-extending portion 135 and the face 125 and a narrower portion 114 between the asymmetrically-extending portion 135 and the adjacent inwardly-facing recess 130. This configuration providing the wide portion 113 near the face 125 along the rim of the shell 100 ensures that a maximum amount of the tapered inner wall 112 surface along the circumference of the shell along the rim is maintained even with the presence of the asymmetrically-extending portions 135 of the recesses 130. In at least one embodiment, the asymmetrically-extending portion 135 is shallower than the main portion 132.

The shell 100 can include any number of inwardly-facing recesses 130. In one embodiment, the shell 100 includes twelve inwardly-facing recesses 130. In another embodiment, the shell 100 includes ten inwardly-facing recesses 130. In another embodiment, the shell 100 includes eight inwardly-facing recesses 130. In another embodiment, the shell 100 includes six inwardly-facing recesses 130. However, any number of inwardly-facing recesses 130 can be included.

In one embodiment, the inwardly-facing recesses 130 extend from the face 125 down into the shell 100 toward the apex in a direction parallel with the central axis A such that each of the inwardly-facing recesses 130 has a contoured sidewall 137 that extends parallel with the central axis A. Because the tapered inner wall 112 is tapered with respect to the central axis A, the sidewalls 137 of the recesses 130 intersect with the tapered inner wall 112 to form a tapered edge 139. When the liner 200 is inserted into the shell 100 and fully assembled, the tapered edge 139 engages the liner 200 to form an interference fit and maintain the liner 200 in place in the shell 100. The tapered edge 139 can form an interference fit with the liner 200 or bite into the liner 200 to secure the liner 200 inside the shell.

Referring to FIG. 3, the inner surface 110 also includes a concave portion 117. The concave portion 117 is defined between the tapered inner wall 112 portion and the apex 127.

The shell 100 includes an annular groove 150 provided between the tapered inner wall 112 and the concave portion 117. The annular groove 150 extends circumferentially, at least partially, around the inner surface 110. In some embodiments, the annular groove 150 extends around the entire circumference. In other embodiments, the annular groove 150 can be segmented such that separate portions of the annular groove 150 are disposed around the circumference.

Figure 5:
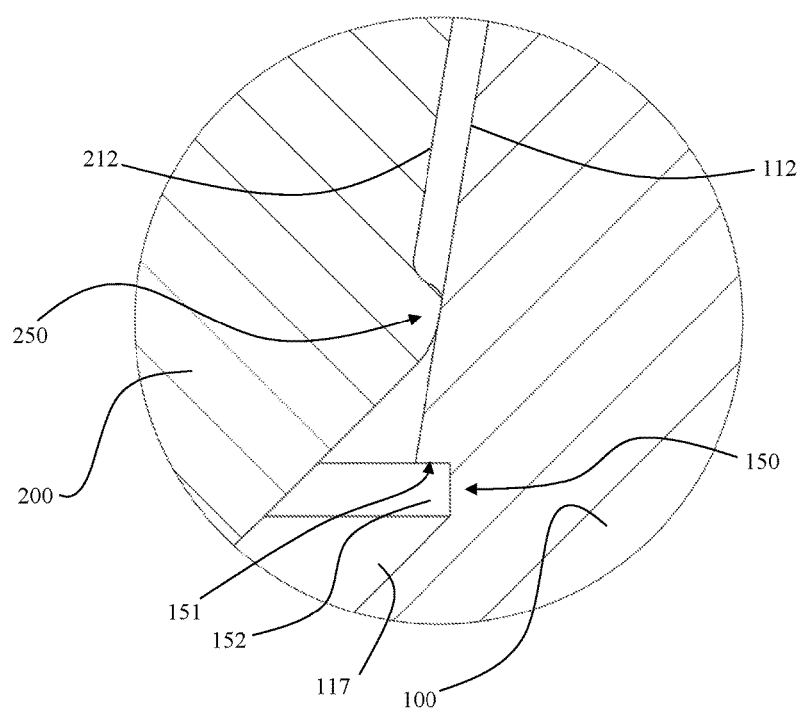
FIG. 5 shows a detailed view of the annular groove provided on the acetabular shell and the annular rib provided on the liner.

The annular groove 150 can include any appropriate geometry. In one embodiment, as shown in FIG. 5, the annular groove 150 includes a top surface 151 which is oriented substantially perpendicularly to the central axis A. As described below, this ensures that the liner 200 and the annular groove 150 engage in a locking manner and prevents unintended removal of the shell 100 from the liner. The annular groove 150 can also include a second surface 152 which is substantially parallel to the central axis. The bottom portion of the annular groove 150 is formed by the concave portion 117.

The liners can generally be constructed of any appropriate material such as ceramic, metal, or polymer. In the embodiments disclosed herein the liner 200 is constructed of a polymeric material such as polyethylene (PE), ultra-high molecular weight polyethylene (UHMWPE), vitamin-E-doped polyethylene, or any other appropriate polymer.

The liner 200 includes additional features to ensure secure engagement with the shell 100. The liner 200 has at least one radial projection 230 provided about the outer periphery of the liner 200. The radial projections 230 are configured for engaging the plurality of inwardly-facing recesses 130 of the shell 100. Each of the radial projections has a main portion 232 and an asymmetrically-extending portion 235 for engaging the corresponding main portion 132 and the asymmetrically-extending portions 135 of the inwardly-facing recesses 130. The engagement of the main portion 232 of the liner with the corresponding main portions 132 of the shell prevents axial rotation of the liner within the shell when the liner 200 is fit within the shell 100. The asymmetrically-extending portions 235 of the liner 200 and the corresponding asymmetrically-extending portions 135 of the shell 100 engage each other to form an interference fit between the shell and the liner when the liner 200 is fitted within the shell 100. This interference fit between the shell and the liner supplements the securement of the two components provided by the annular rib 250 of the liner and the annular groove 150 of the shell described below.

The liner also has an annular rib 250 configured to be received into the annular groove 150 of the shell 100. The annular rib 250 and the annular groove 150 engage each other to prevent axial disassembly of the shell 100 and the liner 200.

Figure 6:
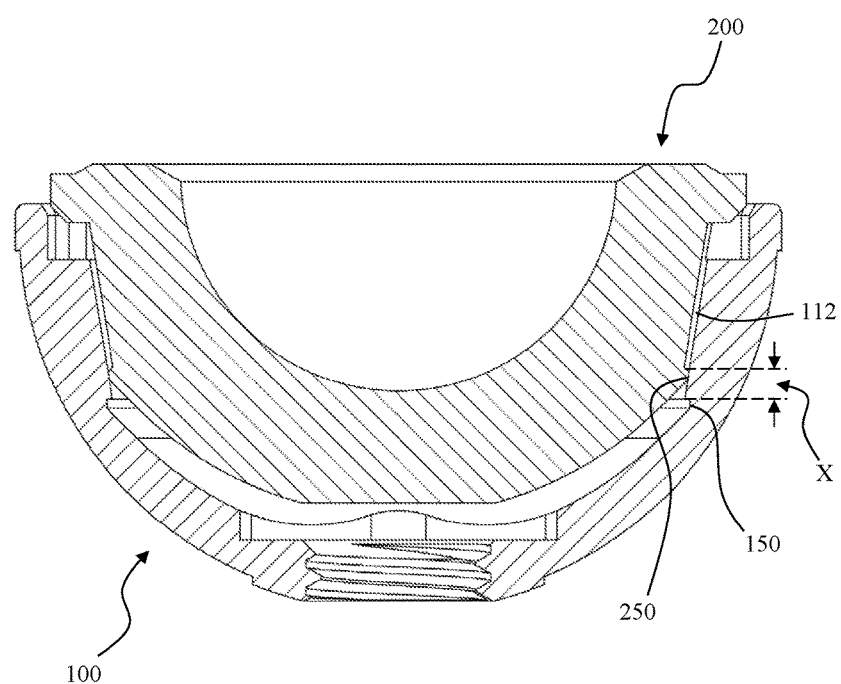
FIG. 6 shows a cross-sectional view of the acetabular shell and the liner with the annular rib of the liner in contact with the tapered inner wall of the shell.

Referring to FIG. 6, the annular rib 250 has an outside diameter which is equal to an inner diameter of the tapered inner wall 112 of the shell 100 at a predefined contact point X from the annular groove 150. This predefined contact point is determined so that as the liner 200 is being inserted into the shell 100 for locking engagement between the annular rib 250 and the annular groove 150, the annular rib contacts the tapered inner wall 112 before the annular rib actually reaches the annular groove. This helps to center the liner 200 in the shell 100 as the liner 200 is being inserted into the shell 100. With the annular rib 250 in contact with the tapered inner wall 112, continued insertion of the liner 200 into the shell 100 will cause the annular rib 250 of the polymeric liner 200 to elastically deform as the annular rib 250 reaches the fully engaged position with the annular groove 150. The physical engagement of the annular rib 250 with the tapered inner wall 112 works in combination with the funnel-like shape of the tapered inner wall 112 portion in guiding the liner into the locking engagement position in the shell 100. Upon being fully inserted, the annular rib 250 engages the annular groove 150 to securely lock the liner 200 in place. In one embodiment, the predefined contact point X from the annular groove 150 to the contact point between the annular rib 250 and the inner wall 112 can be between approximately 0.5 mm and approximately 3.0 mm. In another embodiment, the predefined contact point is between approximately 1.0 mm and approximately 2.0 mm. In another embodiment, the predefined contact point is between approximately 1.2 mm and approximately 1.6 mm. In a preferred embodiment, the predefined contact point X is 1.4 mm.

The outside diameter of the annular rib 250 can be less than the diameter of the second surface 152 of the annular groove 150. As a result, with the liner 200 fully inserted in the shell 100, the annular rib 250 can fit within the annular groove 150 in a natural or uncompressed condition. The first surface 151 of the annular groove 150 prevents the annular rib 250 from exiting the annular groove 150 and, thereby, prevents removal of the liner 200 from the shell 100.

In some embodiments, the inwardly-facing recesses 130 of the shell 100 engage the radial projections 230 of the liner 200 simultaneously with the engagement of the annular rib 250 with the tapered inner wall 112. At this point, the liner 200 is centered within the shell 100 and rotationally aligned due to engagement of the radial projections 230 with the inwardly-facing recesses 130.

In another embodiment, a method for implanting an acetabular cup, according to the embodiments described above, is provided. The method includes the step of providing a shell having an inner surface defining an interior space and a central axis and an outer surface defining an outer hemispherical surface. The shell also includes a face positioned at an upper end of the shell and an apex positioned at a lower end of the inner surface. The inner surface includes a tapered inner wall extending axially and a concave portion defined between the tapered inner wall and the apex. The shell also includes an annular groove positioned between the tapered inner wall and the concave portion. The tapered inner wall extends at least partially around the inner surface.

The method further includes providing a liner for axial securement within the internal cavity of the shell. The liner has an outer surface that is tapered with respect to a central liner axis. The outer surface is compatible with the tapered inner wall of the shell. The liner also has an annular rib at the bottom of the male tapered surface and is configured to be received within the annular groove of the shell. When assembled, the central liner axis coincides with the central axis.

The method includes centering the liner in the shell by axially inserting the liner into the interior space of the shell until the annular rib of the liner engages the tapered inner wall of the shell. At a predefined distance from the annular groove, the tapered inner wall has a diameter that is equal to the outside diameter of the annular rib. As a result, the annular rib contacts the tapered inner wall prior to engaging the annular groove.

The method further includes securing the liner within the shell by further inserting the liner in the axial direction until the annular rib snaps into the annular groove of the shell.

While the foregoing description and drawings represent preferred or exemplary embodiments of the present invention, it will be understood that various additions, modifications and substitutions may be made therein without departing from the spirit and scope and range of equivalents of the accompanying claims. In particular, it will be clear to those skilled in the art that the present invention may be embodied in other forms, structures, arrangements, proportions, sizes, and with other elements, materials, and components, without departing from the spirit or essential characteristics thereof. In addition, numerous variations in the methods/processes described herein may be made without departing from the spirit of the invention. One skilled in the art will further appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims and equivalents thereof, and not limited to the foregoing description or embodiments. Rather, the appended claims should be construed broadly, to include other variants and embodiments of the invention, which may be made by those skilled in the art without departing from the scope and range of equivalents of the invention. All patents and published patent applications identified herein are incorporated herein by reference in their entireties.

What is claimed is:

1. An acetabular cup assembly, comprising:
   a shell, the shell having an inner surface defining an interior space, an outer surface defining an outer hemispherical surface, a face positioned at an upper end of the shell, and an apex positioned at a lower end of the inner surface, the inner surface comprising:
      a tapered inner wall extending from the face toward the apex;
      a plurality of inwardly-facing recesses provided along the inner surface adjacent the face, wherein the plurality of inwardly-facing recesses each have a main portion and an asymmetrically-extending portion;
         the plurality of inwardly-facing recesses interrupting the tapered inner wall and defining a plurality of segmented portions of the tapered inner wall, wherein each segmented portion is located between pairs of adjacent inwardly-facing recesses;
         wherein each asymmetrically-extending portion extends circumferentially in one direction and is spaced apart from the face resulting in each inwardly-facing recess having an asymmetric shape and each segmented portion of the tapered inner wall has a wide portion between an asymmetrically-extending portion and the face and a narrower portion between an asymmetrically-extending portion and a main portion of an adjacent inwardly-facing recess;
      a concave portion defined between the tapered inner wall and the apex; and
   a liner adapted to fit within the interior space and engage the inner surface of the shell establishing an interference fit.

2. The acetabular cup assembly of claim 1, wherein the shell has a central axis and the tapered inner wall of the shell has a taper angle defined with respect to the central axis and the liner has an outer surface that is configured with a male tapered surface that has a second taper angle, wherein the tapered inner wall and the male tapered surface engage to provide the interference fit between the shell and the liner.

3. The acetabular cup assembly of claim 2, wherein the liner is made of a ceramic material or a metal.

4. The acetabular cup assembly of claim 1, wherein the liner is made of a polymeric material.

5. The acetabular cup assembly of claim 1, wherein the liner has a plurality of radial projections provided about its outer periphery for engaging the plurality of inwardly-facing recesses;
   wherein each of the plurality of radial projections has a main portion and an asymmetrically-extending portion for engaging a corresponding main portion and asymmetrically-extending portion of any one of the inwardly-facing recesses,
   wherein corresponding main portions of the liner and shell engage to prevent axial rotation of the liner within the shell when the liner is fit within the shell, and
   wherein corresponding asymmetrically-extending portions of the liner and shell engage to form an interference fit between the shell and the liner when the liner is fit within the shell.

6. The acetabular cup assembly of claim 1, wherein the asymmetrically-extending portion of each inwardly-facing recesses is shallower than the main portion.

7. The acetabular cup assembly of claim 1, wherein the shell further comprises an annular groove provided between the tapered inner wall and the concave portion and extending circumferentially at least partially around the inner surface; and
   the liner having a corresponding annular rib for being received into the annular groove, the annular rib and the annular groove engage each other to prevent axial disassembly of the shell and the liner.

8. An acetabular cup assembly, comprising:
   a shell, the shell having an inner surface defining an interior space, an outer surface defining an outer hemispherical surface, a face positioned at an upper end of the shell, and an apex positioned at a lower end of the inner surface, the inner surface comprising:
      a tapered inner wall extending from the face toward the apex;
      a plurality of inwardly-facing recesses provided along the inner surface adjacent the face, wherein the plurality of inwardly-facing recesses each have a main portion and an asymmetrically-extending portion;
         the plurality of inwardly-facing recesses interrupting the tapered inner wall and defining a plurality of segmented portions of the tapered inner wall, wherein each segmented portion is located between pairs of adjacent inwardly-facing recesses;
         wherein each asymmetrically-extending portion extends circumferentially in one direction and is spaced apart from the face resulting in each inwardly-facing recess having an asymmetric shape and each segmented portion of the tapered inner wall has a wide portion between an asymmetrically-extending portion and the face and a narrower portion between an asymmetrically-extending portion and a main portion of an adjacent inwardly-facing recess;
      a concave portion defined between the tapered inner wall and the apex; and a liner adapted to fit within the interior space and engage the inner surface of the shell establishing an interference fit;

wherein the shell further comprises an annular groove provided between the tapered inner wall and the concave portion and extending circumferentially at least partially around the inner surface; and the liner having a corresponding annular rib for being received into the annular groove, the annular rib and the annular groove engage each other to prevent axial disassembly of the shell and the liner;

wherein at a predefined contact point that is 0.5 to 3.0 mm from the annular groove along the tapered inner wall, the tapered inner wall has an inner diameter that is the same as an outside diameter of the annular rib of the liner so that the annular rib and the tapered inner wall engage each other to center the liner in the shell as the liner is being inserted into the shell before the annular rib snaps into the annular groove for a final seating of the liner.

9. The acetabular cup assembly of claim 8, wherein the predefined contact point is 1.2 to 1.6 mm from the annular groove along the tapered inner wall.

10. The acetabular cup assembly of claim 8, wherein the predefined contact point is 1.4 mm from the annular groove along the tapered inner wall.

11. The acetabular cup assembly of claim 8, wherein the inwardly-facing recesses of the shell and radial projections of the liner engage each other simultaneously as the annular rib snaps into the annular groove.

12. The acetabular cup assembly of claim 8, wherein the liner has an outer surface that is configured with a male tapered surface that has a taper angle that is the same as a taper angle of the shell's tapered inner wall, wherein the male tapered surface and the shell's tapered inner wall engage to provide the interference fit between the shell and the liner.

13. The acetabular cup assembly of claim 8, wherein the liner is made of a polymeric material.

14. An acetabular cup assembly, comprising:

a shell, the shell having an inner surface defining an interior space, an outer surface defining an outer hemispherical surface, a face positioned at an upper end of the shell, an apex positioned at a lower end of the inner surface and a central axis, the inner surface comprising:

a tapered inner wall extending from the face toward the apex, the tapered inner wall being tapered with a taper angle with respect to the central axis;

a plurality of inwardly-facing recesses provided along the inner surface adjacent the face, wherein the plurality of inwardly-facing recesses each have a main portion and an asymmetrically-extending portion;

the plurality of inwardly-facing recesses interrupting the tapered inner wall and defining a plurality of segmented portions of the tapered inner wall, wherein each segmented portion is located between pairs of adjacent inwardly-facing recesses;

wherein each asymmetrically-extending portion extends circumferentially in one direction and is spaced apart from the face resulting in each inwardly-facing recess having an asymmetric shape and each segmented portion of the tapered inner wall has a wide portion between an asymmetrically-extending portion and the face and a narrower portion between an asymmetrically-extending portion and a main portion of an adjacent inwardly-facing recess;

a concave portion defined between the tapered inner wall and the apex; and a liner adapted to fit within the interior space and removably engage the inner surface of the shell establishing an interference fit;

wherein the plurality of inwardly-facing recesses extend from the face of the shell into the shell in a direction parallel with the central axis of the shell so that each inwardly-facing recess has a contoured sidewall that is parallel with the central axis and a tapered edge defined by an intersection of the tapered inner wall of the shell and the contoured sidewall of the each inwardly-facing recess;

wherein the tapered edges and the liner engage to form an interference fit when the liner and the shell are assembled.

15. The acetabular cup assembly of claim 14, wherein the liner is made of a ceramic material or a metal.

16. The acetabular cup assembly of claim 14, wherein the liner is made of a polymeric material.

17. The acetabular cup assembly of claim 14, wherein the liner has an outer surface that is configured with a male tapered surface that has a taper angle that is the same as a taper angle of the shell's tapered inner wall, wherein the male tapered surface and the shell's tapered inner wall engage to provide the interference fit between the shell and the liner.

18. The acetabular cup assembly of claim 14, wherein the liner has a plurality of radial projections provided about its outer periphery for engaging the plurality of inwardly-facing recesses;

wherein each of the plurality of radial projections has a main portion and an asymmetrically-extending portion for engaging a corresponding main portion and asymmetrically-extending portion of any one of the inwardly-facing recesses, wherein corresponding main portions of the liner and shell engage to prevent axial rotation of the liner within the shell when the liner is fit within the shell, and wherein corresponding asymmetrically-extending portions of the liner and shell engage to form an interference fit between the shell and the liner when the liner is fit within the shell.

19. The acetabular cup assembly of claim 14, wherein the asymmetrically-extending portion of each inwardly-facing recesses is shallower than the main portion.

20. The acetabular cup assembly of claim 14, wherein the shell further comprises an annular groove provided between the tapered inner wall and the concave portion and extending at least partially around the inner surface; and the liner having a corresponding annular rib for being received into the annular groove, the annular rib and the annular groove engage each other to establish an interference fit between the shell and the liner.

21. A method for implanting an acetabular cup, comprising the steps of:

providing a shell member having an inner surface defining an interior space and a central axis, an outer surface defining an outer hemispherical surface, a face positioned at an upper end of the shell member, and an apex positioned at a lower end of the inner surface, the inner surface comprising:

a tapered inner wall extending axially and from the face toward the apex;

a plurality of inwardly-facing recesses provided along the inner surface adjacent the face, wherein the plurality of inwardly-facing recesses each have a main portion and an asymmetrically-extending portion;

the plurality of inwardly-facing recesses interrupting the tapered inner wall and defining a plurality of segmented portions of the tapered inner wall, wherein each segmented portion is located between pairs of adjacent inwardly-facing recesses;

wherein each asymmetrically-extending portion extends circumferentially in one direction and is spaced apart from the face resulting in each inwardly-facing recess having an asymmetric shape and each segmented portion of the tapered inner wall has a wide portion between an asymmetrically-extending portion and the face and a narrower portion between an asymmetrically-extending portion and a main portion of an adjacent inwardly-facing recess;

a concave portion defined between the tapered inner wall and the apex, and an annular groove provided between the tapered inner wall and the concave portion and extending at least partially around the inner surface;

providing a liner for axial securement within the interior space, the liner having a central liner axis, an outer surface that is configured with a male tapered surface that is compatible with the tapered inner wall, and an annular rib provided at a bottom end of the male tapered surface for being received into the annular groove of the shell member, the central axis coinciding with the central liner axis when the shell member and the liner are assembled;

centering the liner in the shell member by inserting the liner in an axial direction into the interior space of the shell member until the annular rib of the liner engages the tapered inner wall of the shell member before the annular rib snaps into the annular groove of the shell member; and securing the liner within the shell member by further inserting the liner in an axial direction into the interior space of the shell member until the annular rib snaps into the annular groove of the shell member.

* * * * *